United States Patent [19]

Ruszala et al.

[11] 4,204,261
[45] May 20, 1980

[54] COMPLEX ANALOG SIGNAL GENERATOR

[75] Inventors: Frederick B. Ruszala, Sterling Heights; Kenneth J. Cook, Troy, both of Mich.

[73] Assignee: The Valeron Corporation, Oak Park, Mich.

[21] Appl. No.: 882,357

[22] Filed: Mar. 1, 1978

[51] Int. Cl.² ............... G06T 1/00; G06G 7/26
[52] U.S. Cl. ..................... 364/607; 328/185;
332/31 T; 364/578; 364/851
[58] Field of Search .............. 364/607, 608, 824, 825,
364/718, 851; 307/240; 332/31 T, 59, 68;
328/14, 185, 187; 35/17

[56] References Cited

U.S. PATENT DOCUMENTS

| | | | |
|---|---|---|---|
| 3,110,802 | 11/1963 | Ingham et al. | 364/608 |
| 3,202,940 | 8/1965 | Dietrich | 332/31 T |
| 3,227,892 | 1/1966 | Basham | 332/31 T |
| 3,323,068 | 5/1967 | Woods | 328/187 |
| 3,401,359 | 9/1968 | Becker | 307/240 |
| 3,497,830 | 2/1970 | Colton et al. | 307/240 |
| 3,500,213 | 3/1970 | Ameau | 328/14 |
| 3,543,009 | 11/1970 | Voelcker, Jr. | 364/825 |
| 3,621,221 | 11/1971 | Cann | 364/824 |
| 3,721,836 | 3/1973 | Rippel | 307/240 |
| 3,736,363 | 5/1973 | Baessler et al. | 35/17 |
| 3,793,589 | 2/1974 | Puckette | 364/608 |
| 3,835,403 | 9/1974 | Leineman | 328/14 |
| 3,838,414 | 9/1974 | Wiles | 328/14 |
| 3,935,440 | 1/1976 | Mood et al. | 364/607 |
| 3,938,051 | 2/1976 | Eisenberg | 328/14 |

FOREIGN PATENT DOCUMENTS

| | | |
|---|---|---|
| 982824 | 2/1965 | United Kingdom . |
| 1341912 | 12/1973 | United Kingdom . |
| 1477353 | 6/1977 | United Kingdom . |
| 387386 | 6/1973 | U.S.S.R. ............... 364/607 |

OTHER PUBLICATIONS

Motorola Semiconductors, MC 14017B, Decade/Counter Information Sheet.

Primary Examiner—Felix D. Gruber
Attorney, Agent, or Firm—Krass & Young

[57] ABSTRACT

An electronic circuit for generating complex time-varying analog signal waveforms such as electrocardiogram and blood pressure transducer signals employs analog signal shaping circuits coupled to a summing network to shape the sequential output stage signals of a multiple stage counter and also employs an interface to couple the signal waveforms to external display devices.

20 Claims, 5 Drawing Figures

COMPLEX ANALOG SIGNAL GENERATOR

BACKGROUND OF THE INVENTION

1. Field of the Invention.

This invention relates to electronic circuits for generating complex time-varying analog signal waveforms and more particularly to an electronic circuit which employs digital to analog signal conversion techniques to generate complex time-varying analog signal patterns such as electrocardiogram signals and blood pressure transducer signals.

2. Prior Art.

Many different types of electronic circuits for generating time-varying analog signals are in common use. Circuits for generating sinusoidal waveforms are well known in the art, but the generation of periodic complex waveform is comparatively difficult. One method of generating a periodic complex waveform is by generating a series of harmonically related sinusoidal waveforms and summing the series to thereby produce the complex waveform. Fourier analysis of the particular complex waveform is used to determine the particular frequency, phase and amplitude of each sinusoidal waveform. Since this method requires a plurality of separate signal generating circuits, each producing a waveform having a certain frequency, phase and amplitude, the method is complicated and expensive.

Another method of generating periodic complex waveforms is by using a plurality of circuits, with a separate circuit to generate each specific portion of the waveform. The outputs of the separate circuits are summed to thereby produce the entire complex waveform. However, in order to insure that the periodic relationship between each specific portion of the waveform is correct, it is necessary to detect the completion of the generation of each portion of the waveform before the generation of the next portion. This detection is typically accomplished by sensing the point in time when the amplitude of the preceeding portion of the waveform has crossed a point such as the zero level. The detection of this crossing thereby triggers the succeeding circuit, and this cycle is repeated for each portion of the waveform until the completion of the complex waveform. This method, however, is sensitive to offset levels in the circuitry and requires complex circuitry.

SUMMARY OF THE INVENTION

It is the object of this invention to generate complex time-varying analog signals without the need for multiple signal sources nor waveform amplitude detection means. In general this is accomplished by providing a circuit arrangement which uses a multiple stage counter-divider having output stages that are successively energized so that each stage sequentially provides an exclusive signal at its output, shaping the signal waveform of each output stage to correspond to a particular portion of a complex waveform, and summing the shaped output signals to thereby provide a complex waveform. The entire cycle is repeated to provide a periodic signal. The complex waveforms that are generated may be used to test and calibrate electrocardiogram displays and blood pressure waveform displays.

Further features of the invention include the provision of means for adjusting the period of the complex waveform and means for varying the amplitude of the complex waveform through use of a resistive divider network. Another feature of the invention is an internal calibration circuit for use in selecting the amplitude of the complex waveform and for checking the gain of a display device such as an electrocardiogram monitor. Yet another feature of the invention is the provision of means to interface the complex signal waveforms with different types of blood pressure monitors without the need for a separate external electrical power supply. The preferred embodiment of this invention uses two separate counters, two separate shaping networks and two separate summing networks with both counters controlled by a common clock and a common resetting circuit to produce two separate complex signal waveforms.

DETAILED DESCRIPTION OF THE SPECIFIC EMBODIMENTS

Figure 1:
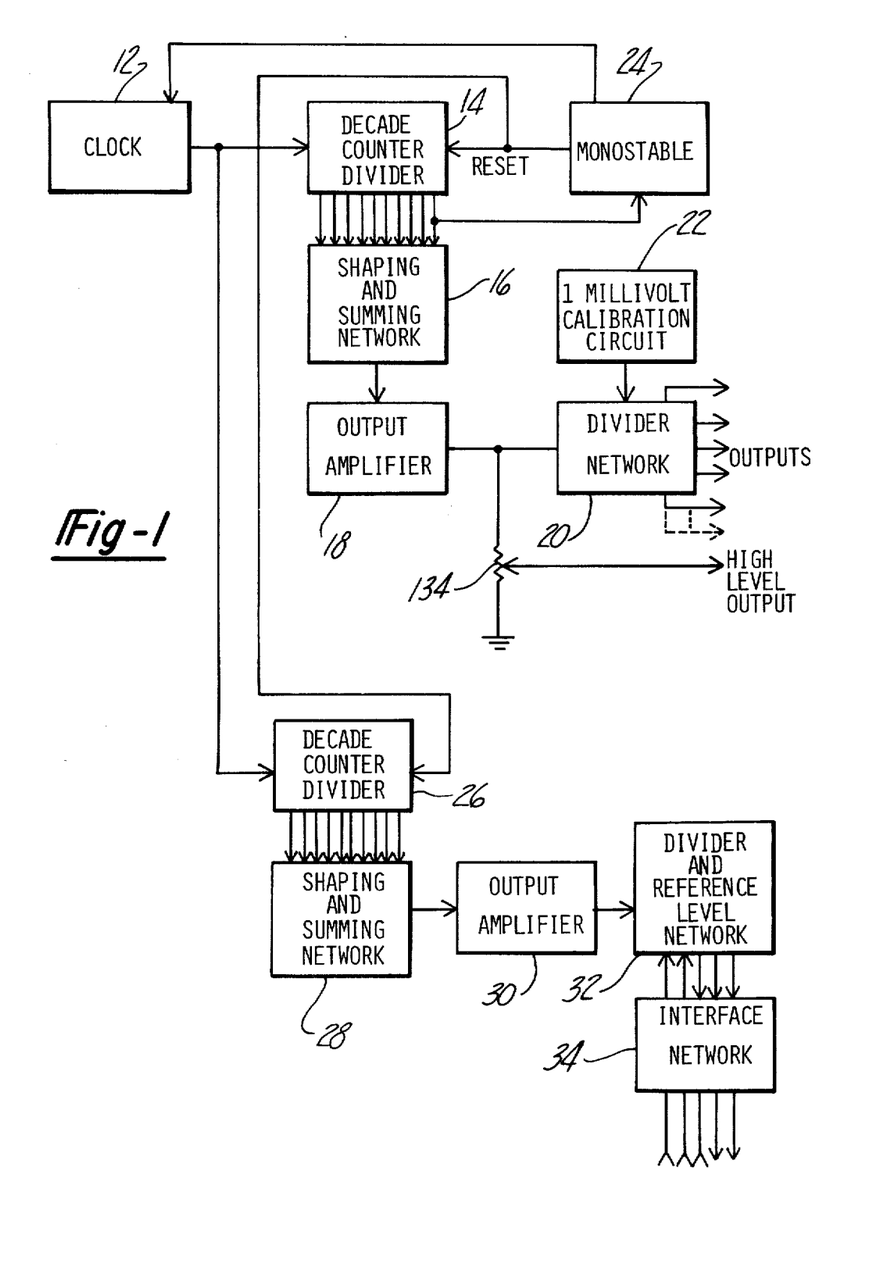
FIG. 1 is a block diagram illustrating a preferred embodiment of our invention.

FIG. 1 discloses a block diagram of an electronic circuit for generating two complex time-varying analog signal waveforms. When the circuit is energized a clock circuit 12 generates a clock signal which is fed to a first decade counter-divider 14. This clock signal causes the counter-divider 14 to count, thereby causing the output stages of the counter-divider 14 to successively change from a LOW state to a HIGH state and back to the LOW state during a specific time period.

Particular output stages of the counter-divider 14 are connected to a first shaping and summing network. The network 16 shapes the particular outputs of the counter-divider 14 to form each particular segment of a desired first complex waveform. The network 16 then sums these segments to produce a complete complex waveform. The output waveform of the network 16 is fed to a first output amplifier 18 and is there amplified.

The output of the amplifier 18 is connected to both a first divider network 20 that divides the waveform into a plurality of outputs having different amplitudes and to a potentiometer 134 for adjusting the high level output. A calibration circuit 22, provides a 1 millivolt reference signal which is fed to the divider network 20. The reference signal is used for checking the gain of a display device to which the first divider network 20 may be connected.

A monostable circuit 24 is used to reset the counter-divider 14 at the end of each signal generating cycle and to disable the clock 12 while the monostable circuit 24 is in its quasi-stable state. The monostable circuit 24 is connected to the counter-divider 14 such that the falling edge of the ninth output stage of the counter-divider 14 triggers the monostable circuit 24. The output of the monostable circuit 24 is fed to the reset input of the counter-divider 14 to thereby reset the counter-divider 14. The monostable circuit 24 utilizes a variable resistive-capacitive network to vary the duration between the receipt of the last output of counter-divider 14 and the output of a reset signal. In this way the period of the entire complex signal can be varied.

The clock 12 and the monostable circuit 24 also control a second decade counter-divider 26. The output of the clock 12 is fed to the clock input of the counter-divider 26, and the output of the monostable circuit 24 is fed to the reset input of the counter-divider 26. The decade counter-divider 26 is utilized to produce a second series of output stage signals which are synchronized to the output stage signals of the first decade counter-divider 12. As with the first decard counter-divider 12, the output stages of the second decade counter-divider 26 change from a LOW state to a HIGH state and back to a LOW state during a specific time period. Particular output stages of counter-divider 26 are connected to a second shaping and summing network 28 which sums and shapes the particular output stage signals. The output of the network 28 is amplified by a second output amplifier 30. The output of the amplifier 30 is divided by a divider and reference level network 32.

The reference level network 32 is connected to and operates in conjunction with an interface network 34 to provide a signal waveform which will be accepted by an external display device.

It is important to note that although this specific embodiment of the invention operates to produce a first output waveform which simulates an electrocardiogram signal, and a second output waveform which simulates a blood pressure transducer signal, many different types of output waveforms may be generated by use of this invention.

Furthermore, although in this specific embodiment of the invention, both counter-dividers 14 and 26 are operated in synchronism, each counter may be operated independently of the other with the use of a separate clock circuit and a separate monostable circuit for each counter-divider.

Figure 2A:
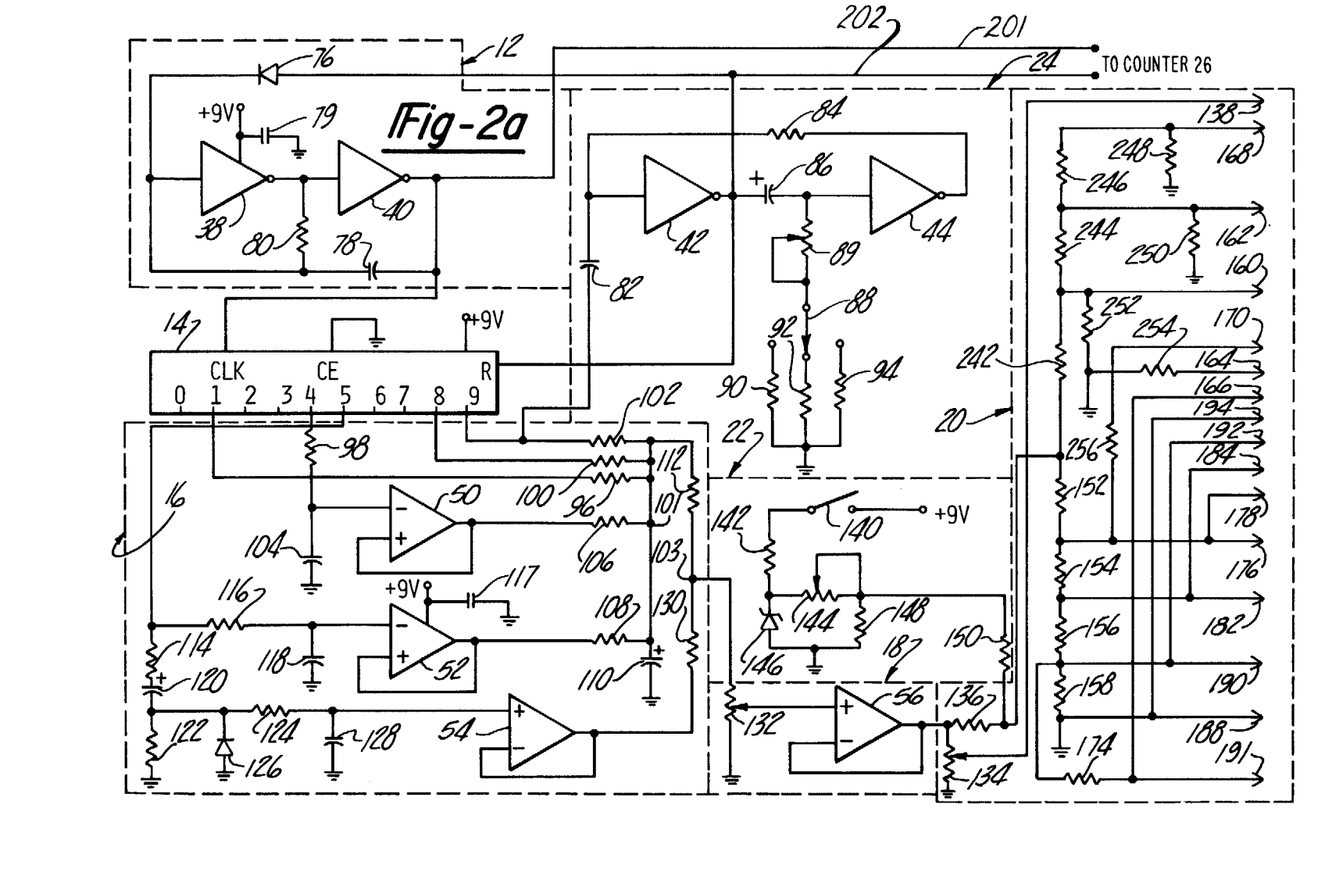
FIGS. 2a and 2b are a detailed schematic diagram of the circuit of FIG. 1.
Figure 2B:
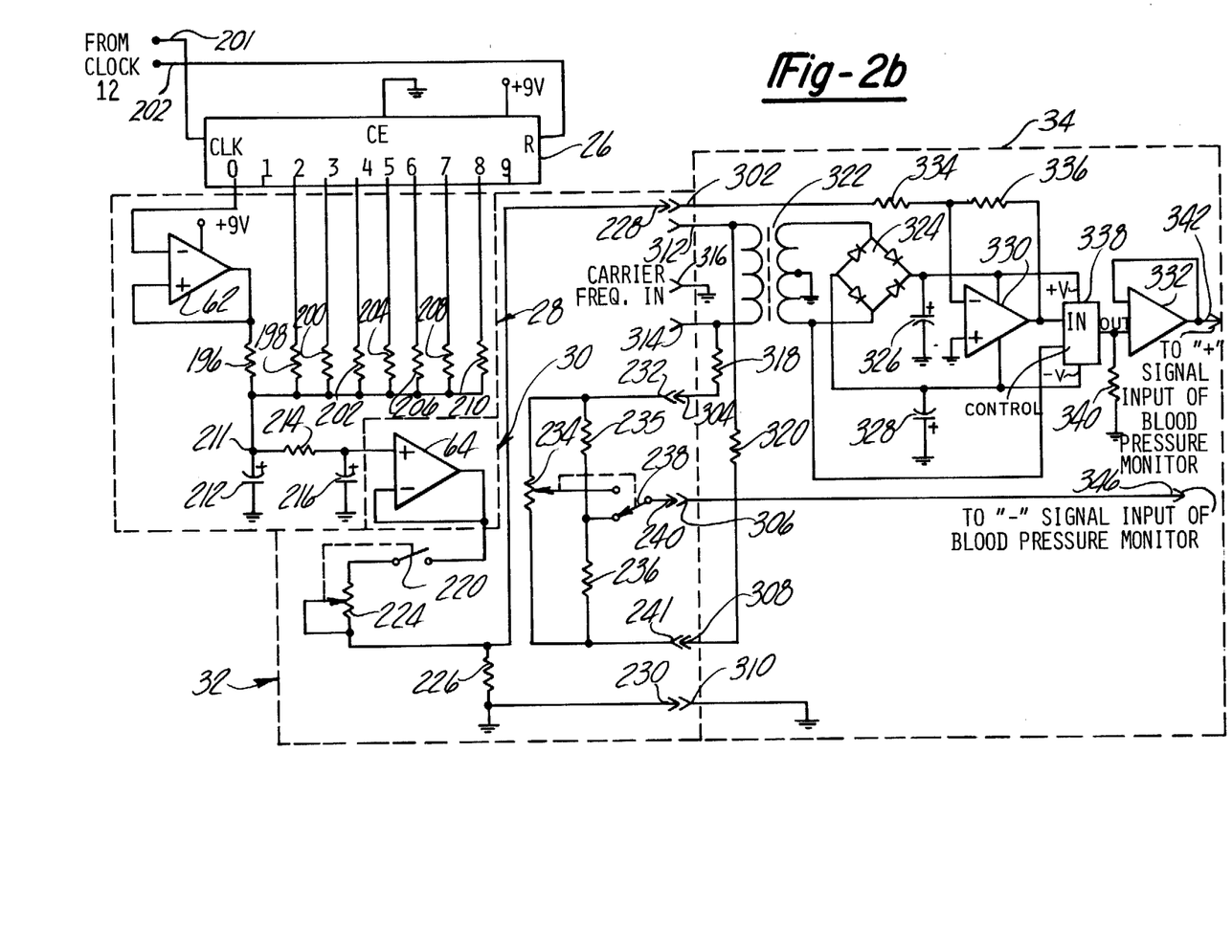

Referring to FIGS. 2a and 2b which disclose the preferred embodiment of the invention in greater detail, the clock 12 employs a pair of inverting amplifiers 38 and 40, with the output of the amplifier 38 connected to the junction of an input of the amplifier 40 and a resistor 80. A resistive-capacitive circuit consisting of the resitor 80 in series with a capacitor 78 determines the frequency of the clock 12. The input of the inverting amplifier 38 is connected to the junction of the resistor 80, the cathode of a diode 76 and the capacitor 78, thereby closing a feedback loop in the clock 12. The power supply input of the inverting amplifers 38 and 40 is bypassed by a capacitor 79.

The output of the clock 12 is fed from the output of the amplifier 40 to a clock input of the first decade counter-divider 14 to thereby actuate the counter-divider 14. In this specific embodiment of the invention the counter-divider 14 is an integrated circuit, although other forms of counters and could be alternately employed. A clock enable input of the counter-divider 14 is grounded. The first, fourth, fifth, eighth and ninth output stages of the counter-divider 14 are shaped and summed by the first summing and shaping network 16.

The summing and shaping network 16 consists of a plurality of subnetworks. A first subnetwork is connected to a first output stage of the counter-divider 14. This first subnetwork utilizes a resistor 96 in series with a capacitor 110 to shape the signal from the first output.

A second subnetwork, connected to a fourth output stage of the counter-divider 14, utilizes a resistor 98 in series circuit with a capacitor 104 to integrate the signal from the fourth output stage. This integrated signal is connected to the negative input of an amplifier 50. The output of amplifier 50 is connected to its positive input as well as the shaping circuit consisting of a resistor 106 in series with the capacitor 110.

A third subnetwork is connected to a fifth output stage of the counter-divider 14. This third subnetwork consists of a differentiator which includes a resistor 114 in series with a capacitor 120, connected between the fifth output stage and the parallel combination of a resistor 122 and a diode 126. The output of this differentiator is further shaped by a series combination of a resistor 124 and a capacitor 128. The output of this series combination is amplified by an amplifier 54. The output of the amplifier 54 is connected to its positive input and to node 103 through a resistor 130.

A fourth subnetwork is also connected to a fifth output stage of the counter-divider 14. This fourth subnetwork consists of a series combination of a resistor 116 and a capacitor 118 followed by an amplifier 52 operating in an inverting mode. The output of the amplifier 52 is connected to its positive input and to the series combination of a resistor 108 and the capacitor 110.

A fifth subnetwork, connected to the eighth output stage of the counter-divider 14, consists of a series circuit of a resistor 100 and the capacitor 100. A sixth subnetwork, connected to the ninth output stage of the counter-divider 14, consists of the series circuit of a resistor 102 and the capacitor 110. The power supply input of amplifiers 50, 52 and 54 is bypassed by a capacitor 117.

The outputs of the first, second, fourth, fifth and sixth subnetworks are connected to the node 103 through a resistor 112. The signal from node 103 is fed to the input of a first output amplifier 56 through a potentiometer 132 and then amplified by the amplifier 56. The output of the amplifier 56 is connected to its negative input and to the input of the divider network 20.

The divider network 20 employs a parallel-series combination of resistors to divide the signal from the output of the amplifier 56 into a plurality of outputs. The input of the divider network 20 is connected to one side of the potentiometer 134. The potentiometer 134 has its other side connected to ground and its center arm connected to an output terminal 138.

The input of the divider network 20 is also connected to a pair of resistive subnetworks through a resistor 136. The first relative subnetwork consists of a plurality of resistors 152, 154, 156, and 158, 174 and 256 in a series arrangement. The second resistive subnetwork consists of a plurality of resistors 242, 244, 246, 248, 250, 252 and 254 in a parallel-series arrangement.

An output terminal 160 is connected to the junction of the resistors 242, 244 and 252. An output terminal 162 is connected to the junction of the resistors 244, 246 and 250 and an output terminal 168 is connected to the junction of the resistors 246 and 248.

The junction of the resistors 152 and 154 is connected in common with a pair of output terminals 176 and 178 and to an output terminal 170 through a resistor 256. The junction of the resistors 154 and 156 is connected in common with a pair of output terminals 182 and 184. The junction of the resistors 156 and 158 is connected in common with a pair of output terminals 190 and 192 and to an output terminal 191 through the resistor 174. A pair of output terminals 188 and 194 are connected to ground.

The monostable circuit 24 employs a pair of inverting amplifiers 42 and 44, with the input of the inverting amplifier 42 coupled to the output of the inverting amplifier 44 through a resistor 84. A capacitor 86, a potentiometer 89 and the diode 76 in conjunction with one of three resistors 90, 92, 94, one such resistor selected by a switch 88, operates as a resistancecapacitance circuit between the output of the inverting amplifier 42 and the input of the inverting amplifier 44, to thereby control the period during which an output of the monostable circuit 24 is in the HIGH state.

As the counter-divider 14 counts, the input of the inverter 42 receives a signal from the ninth output stage of the counter-divider 14 through a capacitor 82. The reception of the signal causes the output of the monostable circuit 24 to change to the HIGH state for a period determined by the resistive-capacitive circuit.

The output of the monostable circuit 24 is fed from the output of the inverter 42 to the reset input of the first counter-divider 14.

The calibration circuit 22 employs the series circuit consisting of a switch 140, a resistor 142 and a zener diode 146 to generate a reference voltage. The voltage across the zener diode 146 is divided by the series combination of a potentiometer 144 and a resistor 148, and this divided voltage is fed through a resistor 150 to the junction of the resistors 136, 152 and 242.

The output of the clock 12 and the output of the monostable circuit 24 are also connected to the clock input and reset input of the second counter-divider 26 respectively. A clockenable input of the counter-divider 26 is grounded.

The zero, second, third, fourth, fifth, sixth, seventh, and eighth outputs of the counter-divider 26 are connected to the second summing and shaping network 28. The zero output is connected to the inverting input of an amplifier 62. The output of the amplifier 62 is connected to its positive input and to a node 211 through a resistor 196.

The second, third, fourth, fifth, sixth, seventh and eighth output stages of the counter-divider 26 are summed at the node 211 by resistors 198, 200, 202, 204, 206, 208 and 210 respectively. The node 211 is connected to the series-parallel circuit consisting of a resistor 214 and a pair of capacitors 212 and 216. This series-parallel circuit shapes the signal at the node 211 and feeds it to the positive input of an amplifier 64.

The output of the amplifier 64 is connected to its negative input and is also fed through switch 220 to a series resistive divider network consisting of a resistor 226 and a potentiometer 224. An output terminal 228 is connected to the junction of the potentiometer 224 and the resistor 226.

A potentiometer 234 and a pair of resistors 235 and 236 divide a signal across a pair of input terminals 232 and 241. The divided signal is selected through a switch 238 and fed to an output terminal 240.

The interface network 34 utilizes a plurality of input terminals 302, 306, 310, 312, 314 and 316 and a plurality of output terminals 304, 308, 342 and 346. The input terminals 302, 306 and 310 are connected to the output terminals 228, 240 and 230 respectively. The output terminals 304 and 308 are connected to the input terminals 232 and 241 respectively. The input terminals 312, 314 and 316 are connected to the carrier frequency output of an external blood pressure monitor, and the output terminals 342 and 346 are connected to the positive and negative differential inputs respectively of the external blood pressure monitor. The input terminal 306 is connected to the output terminal 346.

The input terminals 312 and 314 are also connected to a pair of resistors 318 and 320 respectively and to the primary of a transformer 322. The secondary of the transformer 322 has its center tap grounded and its two output leads connected to a bridge rectifier 324.

The output of the bridge rectifier 324 is filtered by a pair of capacitors 326 and 328, and powers a pair of amplifiers 330 and 332 and an analog switch 338. A resistor 334 connects the terminal 302 to the junction of the negative input of the amplifier 330 and a feedback resistor 336. The output of the amplifier 330 is fed to the other side of the resistor 336 and to the input of the analog switch 338.

One side of the secondary of the transformer 322 is also connected to the control terminal of the analog switch 338. The output of the analog switch 338 is connected to the junction of a resistor 340 and the positive input of the amplifier 332. The output of the amplifier 332 is connected to its negative input and to the output terminal 342.

Figure 4:
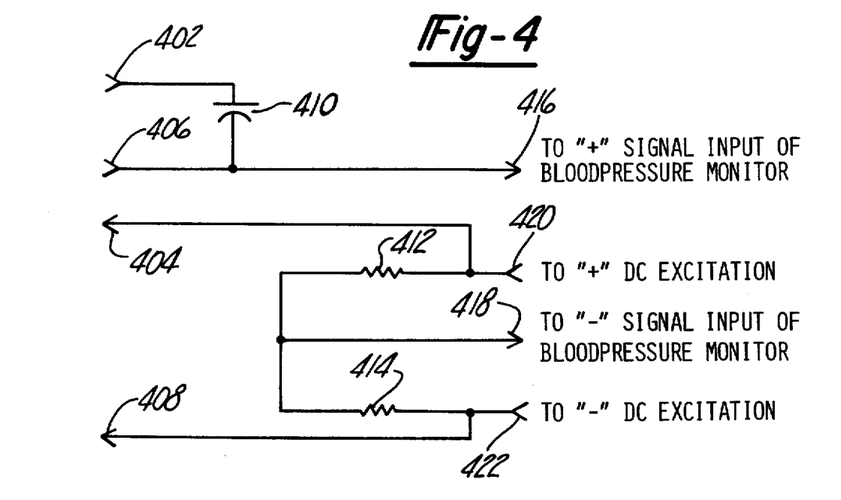
FIG. 4 is a detailed schematic diagram of an alternative embodiment of an interface network.

Referring to FIG. 4 the alternative embodiment of the interface network includes a plurality of input terminals 402, 406, 420 and 422 and a plurality of output terminals 404, 408, 416 and 418. A capacitor 410 is connected between the terminal 402 and the junction of the terminals 406 and 416. The terminal 418 is connected to the junction of a pair of resistors 412 and 414. The other side of the resistor 412 is connected to the junction of the terminals 404 and 420, and the other side of the resistor 414 is connected to the junction of the terminals 408 and 422.

OPERATION

Figure 3:
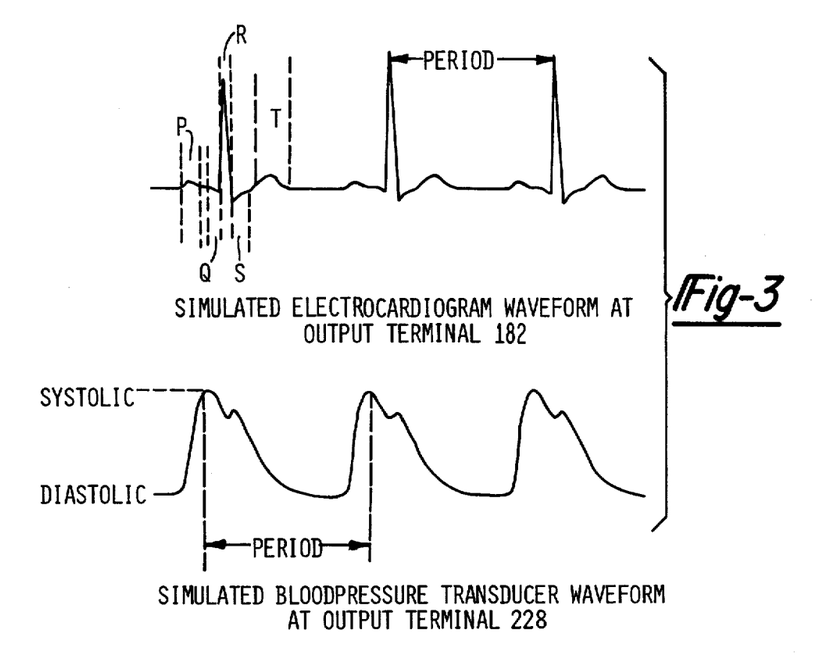
FIG. 3 depicts the two output signal waveforms of the preferred embodiment of our invention.

Referring to FIGS. 2a, 2b and 3, when the circuit is energized, the inverting amplifiers 38 and 40 operate to generate a clock signal having a frequency of 25.0 Hertz, ±0.5 Hertz.

This clock signal is connected to the clock input of the first decade counter-divider 14, and thereby controls a counting action. As the first decade counter-divider 14 counts, each of its output stages successively changes from a LOW state to a HIGH state, then returns to a LOW state in its appropriate time period.

The first form of complex signal chosen for this embodiment is that electrical signal produced by a human heart. As the first output stage of the counter-divider 14 goes HIGH the "P" wave in FIG. 3 is formed through the action of the capacitor 110 and the resistor 96.

The "Q" wave in FIG. 3 is derived by integrating the signal of the fourth output stage of the counter-divider 14 with the resistor 98 and the capacitor 104, then inverting the integrated signal with the amplifier 50. The output of the amplifier 50 is summed through the resistor 106 at the node 101.

Because the "R" wave in FIG. 3 has steep rising and falling edges, it is generated by differentiating the signal of the fifth output stage of the counter-divider 14 through the capacitor 120 and the resistor 122 and then shaping the differentiated signal with the resistor 124 and the capacitor 128. The diode 126 operates to cause the capacitor 120 to recover quickly. The shaped signal is then buffered by the amplifier 54 and summed with the other waves through the resistor 130 at node 103.

The "S" wave in FIG. 3 is generated by shaping the signal of the fifth output stage of the counter-divider 14 with the resistor 116 and the capacitor 118. This shaped signal is inverted by the amplifier 52 and summed by the resistor 108 at the node 101.

The last wave of the first complex signal is the "T" wave in FIG. 3. The "T" wave has a longer duration than any of the other segments, therefore requiring that both the eighth and ninth output stages of the counter-divider 14 be used for its generation. The signal from the eighth output stage is summed by the resistor 100 at node 101, and the signal from the ninth output stage is summed by the resistor 102 at the node 101.

The "Q", "S", and "T" waves are further shaped at the node 101 by the integrating action of the capacitor 110. The node is coupled to the node 103 through the resistor 112 to thereby sum the "P", "Q", "S" and "T" waves with the "R" wave.

The falling edge of the signal from the ninth stage of the counter-divider 14 is fed through the capacitor 82 to thereby trigger the monostable circuit 24. During the time that the monostable circuit 24 is in its quasi-stable state, the reset input of first decade counter-divider 14 is in a HIGH state, thereby preventing any counting action.

In order to insure that the rate stability of the clock 12 is maintained during the time that the monostable circuit 24 is in its quasi-stable state, the diode 76 operates to inhibit the operation of the clock 12. Thus, by using the capacitor 86, the switch 88, the potentiometer 89 and the resistors 90, 92 and 94 to control the duration during which the monostable circuit 24 is in its quasi-stable state, the period of the complex signal may be varied. This, for example, allows different heartbeat rates to be obtained. In the preferred embodiment of the invention the resistors 90, 92 and 94 are selected to provide heartbeat rates of 120, 90 and 60 beat per minute. The potentiometer 89 is adjusted to compensate for the variation in value of the capacitor 86.

To provide a proper output signal level the first divider network 20 is used. The potentiometer 132 adjusts the amplitude of the complex signal into the input of the buffer amplifier 56. The potentiometer 134 provides an adjustable high level output at the output terminal 138. The resistor 136 couples the output of the buffer amplifier 56 to the resistive divider network consisting of the resistors 152, 154, 156, 158, 174 and 256. In typical operation the potentiometer 132 is adjusted to provide a 1 millivolt output between the output terminals 182 and 190. Since all electrocardiogram monitors utilize a 1000:1 amplifier, this 1 millivolt output would produce a 1 volt signal within an electrocardiogram monitor.

The output of the buffer amplifier 56 is also coupled to the resistive divider network consisting of the resistors 242, 244, 246, 248 250, 252 and 254. The output terminals 160, 162, 164, 166, 168 and 170 are designated V4, V5, V2, V1, V6 and V3 respectively in accordance with the terminology adopted by the American College of Cardiology.

In a typical application output terminals designated V1, V2, V3, V4, V5 and V6 are connected to a three channel electrocardiogram monitor. The output terminals designated V1, V2, V3, V4, V5 and V6 are connected to the resistive divider network in a manner so as to provide different potentials of the same output signal to thereby simulate typical electrocardiogram signals.

The calibration circuit 22 utilizes the zener diode 146 and the current limiting resistor 142 to produce a reference voltage across the zener diode 146. This reference voltage is divided by the potentiometer 144 and the resistor 148. The potentiometer 144 is adjusted to provide a 1 millivolt output across the terminals 176 and 182. This calibration circuit permits calibration of an electrocardiogram monitor.

The second form of complex signal included in this embodiment and depicted in FIG. 3 is that electrical signal having the same waveform as a signal produced by a blood pressure transducer. The peak value of the signal represents the systolic pressure, and the lowest value of the signal represents the diastolic pressure. This second complex signal is generated in essentially the same manner as the first complex signal. The clock signal from the output of inverter 40 actuates the clock input of the second decade counter-divider 26. The reset signal from the output of inverter 42 resets the reset input of the second decade counter-divider 26.

As the second decade counter-divider 26 counts, each one of its output stages changes from the LOW state to the HIGH state then back to the LOW state during its appropriate time period.

Since a blood pressure transducer waveform is a continuous waveform with no rapid rise times, as shown in FIG. 2, the zero, second, third, fourth, fifth, sixth, seventh and eighth output stages of the second decade counter-divider 26 are used to generate the waveform. In order to achieve a rounded leading edge, the zero output stage is inverted by the amplifier 62 and summed by the resistor 196 at node 211. The second, third, fourth, fifth, sixth, seventh and eighth output stages are summed at the node 211 by the resistors 198, 200, 202, 204, 206, 208 and 210 respectively.

The summed signal at the node 211 is then shaped by the capacitors 212 and 216 and the resistor 214. The shaped signal is amplified by the buffer amplifier 64. The output of the amplifier 64 is divided by the dividing network consisting of the resistor 226 and the potentiometer 224. The potentiometer 224 controls the amplitude of the second complex waveform between the output terminals 228 and 230.

In order to provide a signal compatible with alternating current excitation type blood pressure monitors, the interface network 34 shown in FIG. 2b is used. An important feature of the network is that is utilizes the carrier frequency signal from the blood pressure monitor to power the interface network circuitry. Since the preferred embodiment of the invention, the interface network is detachable from the remainder of the circuit, an independent power source for the interface network is desirable.

In normal operation a carrier frequency signal from an alternating current excitation tupe blood pressure monitor is fed into the input terminals 312, 314 and 316 to the primary of the transformer 322. The transformer primarily serves to isolate the monitor to insure that the carrier frequency signal is not unduly loaded. The secondary winding of the transformer 322 is applied to the bridge rectifier 324. The bridge rectifier 324 provides both a positive and negative direct current voltage with reference to the ground center-tap of the transformer 324. The capacitor 326 and the capacitor 328 filter the positive and negative voltages respectively, and these voltages are used to power the amplifiers 330 and 332 and the analog switch 338.

The simulated blood pressure signal from the terminal 228 is fed through the terminal 302 and the resistor 334 to the negative input of the amplifier 330. The output of the amplifier 330 provides an inverted signal to the input of the analog switch 338. The control terminal of the analog switch 338 is fed the carrier frequency signal from the secondary winding of the transformer 322. The analog switch 338 is utilized as a chopper to thereby modulate the amplitude of the carrier frequency signal with the simulated blood pressure signal. The modulated carrier frequency signal is then fed from the output of the analog switch 338 to the buffer amplifier 332. The buffer amplifier 332 provides a low impedance output at terminal 342. By providing a low impedance output at terminal 342 the interface network 34 is more versatile since its operation is less dependent upon the input impedance of a blood pressure monitor.

The resistors 318 and 320 operate as one leg of a resistive bridge circuit, the other leg consisting of either the potentionmeter 234 and the resistors 235 and 236. The values of the resistors 235 and 236 are selected to match a particular setting of the center arm of the potentiometer 234. In operation the center arm of the potentiometer 234 is adjusted to provide an offset at the differential input of a blood pressure monitor. The offset level thereby determines the diastolic pressure reading on the monitor.

An alternative embodiment of an interface network is shown in FIG. 4. The newtork of FIG. 4 is utilized instead of that is FIG. 2b whenever a particular blood pressure monitor utilizes direct current excitation instead of alternating current excitation. The capacitor 410 couples the blood pressure signal to the monitor. The resistors 412 and 414 operate as one leg of a resistive bridge network, and thereby prevent the potentiometer 234 to be adjusted to provide a desired offset level. As with the other embodiment of interface network, the offset level determines the diastolic pressure reading on the monitor. The values of the resistors 412 and 414 are chosen to match the requirements of a particular brand of direct current excitation type blood pressre monitor.

The following component values have been found satisfactory for an operative embodiment of the invention. All resistors are 0.25 watt, 5% unless otherwise indicated.

The invention has been described with reference to a specific embodiment and specific component values, and it is to be understood that although this embodiment represents the best mode of practicing the invention known to the inventor at the time of filing the patent application, various modifications and additions to the illustrated embodiment are possible and accordingly the foregoing description is not to be construed in a limiting sense.

We claim:

1. An electronic circuit for generating a simulated complex time-varying biological signal waveform, comprising:
    counter means having a plurality of stages for sequentially providing a uniform digital output signal to each stage;
    clock means for regularly advancing the state of the counter wherein said digital signal is exclusively provided to only one stage at a time;
    a plurality of analog signal shaping circuits each having an input and output, with each input connected to a stage of the counter so that each shaping circuit is sequentially energized by the digital output signal from its corresponding counter stage, said shaping circuits generating segments of a simulated electrocardiogram waveform, with one of said shaping circuits including a resistive-capacitor integrator for shaping the output of one stage of the counter into electrocardiogram P-segment; and
    summing means connected to the outputs of each of the analog signal shaping circuits whereby the summing means provides a time-varying analog signal simulating an electrocardiogram waveform as its output.

2. The electronic circuit of claim 1 wherein the simulated biological waveform is a blood pressure waveform.

3. The electronic circuit of claim 1 wherein one of said signal shaping circuits shapes an output of said counter into a Q segment of said electrocardiogram waveform and comprises:
    a resistive-capacitive integrator having an input and an output; and
    an inverting amplifier connected to the output of said resistive-capacitive integrator.

4. The electronic circuit of claim 1 wherein one of said analog signal shaping circuits shapes an output of said counter into an R segment of an electrocardiogram waveform and comprises:
    a resistive-capacitive differentiator having an input and an output;
    a unidirectional conductive means connected to the output of said resistive-capacitive differentiator; and
    a resistive-capacitive integrator connected to the output of said resistive-capacitive differentiator.

5. The electronic circuit of claim 1 wherein one of said analog signal shaping circuits shapes an output of said counter into the S segment of an electrocardiogram waveform and comprises:
    a resistive-capacitive integrator having an input and an output; and
    an inverting amplifier having an input connected to the output of said resistive-capacitive integrator.

6. The electronic circuit of claim 1 wherein one of said analog signal shaping circuits shapes at least two outputs of said counter into the T segment of an electrocardiogram waveform and comprises:
    a resistive-capacitive integrator having two inputs and one output.

7. The electronic circuit of claim 1 wherein the summing means comprises:
    a plurality of resistors having a common node connected to the output of each of said analog signal shaping circuits.

8. The electronic circuit of claim 1 wherein said clock means includes oscillator means for providing a plurality of clock signals to said counter, said oscillator means having a disenable input for preventing generation of said clock signals and wherein said circuit further comprises:
    means for providing a disabling signal to the disenable input of said oscillator for temporarily preventing further generation of the clock signals thereby defining discrete periods for the generated waveforms.

9. The electronic circuit of claim 8 which further includes:
    monostable means coupled between the last stage of the counter and the disenable input of the oscillator, with said monostable means being triggered upon receipt of a signal from the last stage and providing a signal of a given duration to said oscillator to inhibit operation thereof; and
    adjustable resistive-capacitive means coupled to said monostable means for controlling the duration of its output signal whereby the period of the waveform may be changed by adjustment of said resistive-capacitive means.

10. The electronic circuit of claim 1 which further comprises:
  second counter means having a plurality of states for sequentially providing a uniform digital output signal to each stage;
  a second plurality of analog signal shaping circuits each coupled to a stage counter for generating a simulated blood pressure waveform; and
  means for coupling the output of the block means to said second counter so that the simulated electrocardiogram and blood pressure waveforms are generated in synchronization.

11. The electronic circuit of claim 10 wherein one of the analog signal shaping circuits for shaping the blood pressure waveform comprises:
  an inverter coupled to the output of one stage, with the output of the inverter being connected to a resistor.

12. The electronic circuit of claim 11 wherein the other analog signal shaping circuits for generating the blood pressure waveform comprise resistive networks.

13. The electronic circuit of claim 12 wherein the outputs of all of the analog signal shaping circuits for generating the blood pressure waveform are summed together and then shaped by a resistive-capacitive network.

14. The electronic circuit of claim 10 which further comprises:
  means coupled to the last output stage of the first counter for resetting said first and second counters.

15. The electronic circuit of claim 14 wherein said reset means comprises:
  monostable means for generating a signal of a given duration upon receipt of a triggering signal from the last counter output stage, said monostable signal being coupled to a reset input of said first and second counters, and to a disabling input of the clock means.

16. An electronic circuit for generating a simulated electrocardiogram waveform, comprising:
  multistage counter means for sequentially providing an output signal at each stage;
  a plurality of analog signal shaping circuits each coupled to a stage of the counter, said shaping circuits including:
  a resisitive-capacitive integrator to form a P segment of said simulated electrocardiogram waveform;
  a resistive-capacitive integrator having an input and output, and an inverting amplifier connected to the output of said resistive-capacitive integrator to form a Q segment of said simulated electrocardiogram waveform;
  a resisitive-capacitive differentiator having an input and an output, a unidirectional conductive means connected to the output of said resistive-capacitive differentiator, and a resistive-capacitive integrator connected to the output of said resistive-capacitive differentiator to form an R segment of said simulated electrocardiogram waveform;
  a resistive-capacitive integrator having an input and an output, and an inverting amplifier having an input connected to the output of said resistive-capacitive integrator to form an S segment of said simulated electrocardiogram waveform;
  a resistive-capacitive integrator having two inputs and one output to form a T segment of said simulated electrocardiogram waveform; and
  means for summing the outputs of the analog signal shaping circuits to provide a completed simulated electrocardiogram waveform.

17. An electronic circuit for generating a simulated time-varying signal waveform to test the operation of a remote device, comprising:
  a counter having a plurality of stages;
  means for regularly advancing the stage of the counter;
  a plurality of analog signal shaping circuits each having an input and output, with each input connected to a stage of the counter;
  summing means connected to the outputs of each of the analog signal shaping circuits whereby the summing means provides a simulated time-varying analog signal waveform as its output; and
  an interface connected between said summing means and the remote device operative to thereby modulate a carrier frequency signal received from the remote device with said time-varying signal waveform for transmission to the remote device.

18. The electronic circuit of claim 17 wherein said interface comprises:
  analog switch means operative to modulate said carrier frequency signal with said time-varying signal waveform; and
  power supply means operative to rectify said carrier frequency signal and thereby power said analog switch means.

19. An electronic circuit for generating a simulated waveform for testing a remote device, comprising:
  a counter having a plurality of stages;
  means for regularly advancing the stage of the counter;
  a plurality of analog signal shaping circuits each having an input and output, with each input connected to a stage of the counter;
  summing means connected to the outputs of each of the analog signal shaping circuits whereby summing means provides a simulated time-varying analog signal waveform as its output;
  a divider network coupled to the summing means and having a plurality of resistive legs for supplying said simulated signal at selected levels to the remote device; and
  calibration means connected to the summing means operative to generate a reference signal at the output of a selected resistive leg pair wherein said remote device may be calibrated.

20. In a biological waveform simulator device, an electronic circuit for modulating a carrier frequency signal with an information containing signal for transmission to a remote device, comprising:
  analog switch means having two signal inputs and a power supply input for energizing components thereof, said switch means operative to amplitude modulate said carrier frequency signal on one input with said information signal on the other input wherein the amplitude modulated signal is transmitted to the remote device; and
  power supply means operative to rectify said carrier frequency signal and coupling the rectified output to the power supply input of the switch means to thereby power said analog switch means.

* * * * *